United States Patent
Ikemoto et al.

(10) Patent No.: US 11,964,042 B2
(45) Date of Patent: Apr. 23, 2024

(54) ADDITIVE FOR MEDICINAL AGENTS

(71) Applicant: NIPPON SHOKUBAI CO., LTD., Osaka (JP)

(72) Inventors: Yui Ikemoto, Osaka (JP); Yuko Toba, Osaka (JP); Masahiro Nakanosho, Osaka (JP); Hirokazu Niwa, Osaka (JP)

(73) Assignee: NIPPON SHOKUBAI CO., LTD., Osaka (JP)

( * ) Notice: Subject to any disclaimer, the term of this patent is extended or adjusted under 35 U.S.C. 154(b) by 176 days.

(21) Appl. No.: 17/601,879

(22) PCT Filed: Apr. 27, 2020

(86) PCT No.: PCT/JP2020/017902
§ 371 (c)(1),
(2) Date: Oct. 6, 2021

(87) PCT Pub. No.: WO2020/230600
PCT Pub. Date: Nov. 19, 2020

(65) Prior Publication Data
US 2022/0202688 A1    Jun. 30, 2022

(30) Foreign Application Priority Data

May 14, 2019   (JP) ................ 2019-091541

(51) Int. Cl.
  *A61K 8/81*    (2006.01)
  *A61Q 19/00*   (2006.01)
  *C08F 26/06*   (2006.01)

(52) U.S. Cl.
  CPC ............ *A61K 8/8182* (2013.01); *A61Q 19/00* (2013.01); *C08F 26/06* (2013.01); *A61K 2800/10* (2013.01); *A61K 2800/412* (2013.01)

(58) Field of Classification Search
  CPC ................ A61K 8/8182; A61K 2800/412
  See application file for complete search history.

(56) References Cited

U.S. PATENT DOCUMENTS

| | | | |
|---|---|---|---|
| 11,000,636 B2 | 5/2021 | Ushiro et al. | |
| 2019/0224644 A1 | 7/2019 | Ikemoto et al. | |
| 2019/0255227 A1 | 8/2019 | Ushiro et al. | |
| 2019/0300629 A1 | 10/2019 | Ikemoto et al. | |
| 2019/0315960 A1 | 10/2019 | Kemoto et al. | |

FOREIGN PATENT DOCUMENTS

| | | |
|---|---|---|
| JP | 2004-161829 A | 6/2004 |
| JP | 2010-254974 A | 11/2010 |
| JP | 2013-521364 A | 6/2013 |
| JP | 2017-052911 A | 3/2017 |
| JP | 2018-104406 A | 7/2018 |
| WO | 2018/061916 A1 | 4/2018 |

OTHER PUBLICATIONS

Machine translation of JP2018-104406, provided by espacenet.com (Year: 2023).*
Machine translation of JP2004-161829, provided by espacenet.com (Year: 2023).*
International Search Report issued in corresponding International Patent Application No. PCT/JP2020/017902 dated Jul. 21, 2020 (5 pages).
Written Opinion issued in corresponding International Patent Application No. PCT/JP2020/017902 dated Jul. 21, 2020 (4 pages).
Office Action issued in counterpart Japanese Patent Application No. JP 2021-519352 A dated Nov. 15, 2022 (4 pages).
Extended European Search Report issued in European Application No. 20806324.8, dated Jun. 7, 2023 (10 pages).

* cited by examiner

*Primary Examiner* — Alexandre F Ferre
(74) *Attorney, Agent, or Firm* — Osha Bergman Watanabe & Burton LLP

(57) ABSTRACT

Provided is an additive for a chemical agent, which is capable of improving the functions of various chemical agents. The additive for a chemical agent according to an embodiment of the present invention includes a polymer (I) containing 50 mol % to 100 mol % of a structural unit derived from an N-vinyl lactam-based monomer with respect to 100 mol % of structural units derived from all monomers, the additive for a chemical agent having an average particle diameter of 100 μm or less in a state of having been dried under a reduced pressure of 0.02 MPa or less at 100° C. for 1 hour.

5 Claims, No Drawings

ADDITIVE FOR MEDICINAL AGENTS

TECHNICAL FIELD

The present invention relates to an additive for a chemical agent.

BACKGROUND ART

Chemical agents express various functions, and are used for, for example, a cosmetic, a fragrance, an aromatic, a deodorant, a pharmaceutical, an insect repellent, an insecticide, and an agricultural chemical. Such chemical agent generally contains a functional component for expressing its function. However, among such chemical agents, there are, for example, chemical agents having low persistence of various effects, such as a sensation of coolness (low sustained-release property), and chemical agents that give poor feeling.

In recent years, there has been reported a gelling agent for a sustained-release chemical agent, which is used by absorbing a sustained-release chemical agent, and is excellent in liquid absorption capacity, the gelling agent being also capable of imparting an excellent sustained-release property (Patent Literature 1).

CITATION LIST

Patent Literature

[PTL 1] JP 2017-52911 A

SUMMARY OF INVENTION

Technical Problem

The applicant of the present application has made extensive investigations in order to develop a novel additive capable of improving the functions of various chemical agents. As a result, the applicant has found that an additive containing a specific polymer and having specific physical properties can improve the functions of various chemical agents. Thus, the present invention has been completed.

An object of the present invention is to provide an additive for a chemical agent, which is capable of improving the functions of various chemical agents.

Solution to Problem

According to one embodiment of the present invention, there is provided an additive for a chemical agent, including a polymer (I) containing 50 mol % to 100 mol % of a structural unit derived from an N-vinyl lactam-based monomer with respect to 100 mol % of structural units derived from all monomers, the additive for a chemical agent having an average particle diameter of 100 μm or less in a state of having been dried under a reduced pressure of 0.02 MPa or less at 100° C. for 1 hour.

In one embodiment, an average particle diameter of a swelled body obtained by swelling the additive for a chemical agent according to the one embodiment of the present invention with deionized water is 180 μm or less.

In one embodiment, the polymer (I) is a polymer obtained by precipitation polymerization.

In one embodiment, the additive for a chemical agent is an additive for a cosmetic.

Advantageous Effects of Invention

According to the present invention, the additive for a chemical agent, which is capable of improving the functions of various chemical agents, can be provided.

DESCRIPTION OF EMBODIMENTS

When the expression "weight" is used herein, the expression may be replaced with "mass" that is commonly used as an SI unit representing a weight.

<<Additive for a Chemical Agent>>

An additive for a chemical agent according to an embodiment of the present invention may be used for any appropriate chemical agent to such an extent that the effect of the present invention is not impaired. Examples of such chemical agent include a cosmetic, a fragrance, an aromatic, a deodorant, a pharmaceutical, an insect repellent, an insecticide, and an agricultural chemical, and a typical example is a cosmetic. That is, the additive for a chemical agent according to the embodiment of the present invention is typically an additive for a cosmetic.

The chemical agent may contain an alcohol. When the chemical agent contains the alcohol, the content of the alcohol is preferably from 30 wt % to 100 wt %, more preferably from 50 wt % to 100 wt %, still more preferably from 60 wt % to 100 wt %, particularly preferably from 70 wt % to 100 wt % with respect to 100 wt % of the chemical agent. Any appropriate alcohol may be adopted as the alcohol to such an extent that the effect of the present invention is not impaired.

The additive for a chemical agent includes a polymer (I) containing 50 mol % to 100 mol % of a structural unit derived from an N-vinyl lactam-based monomer with respect to 100 mol % of structural units derived from all monomers.

From the viewpoint that the effect of the present invention can be further expressed, the content of the polymer (I) in the additive for a chemical agent is preferably from 50 wt % to 100 wt %, more preferably from 70 wt % to 100 wt %, still more preferably from 90 wt % to 100 wt %, particularly preferably from 95 wt % to 100 wt %, most preferably substantially 100 wt % with respect to 100 wt % of the additive for a chemical agent.

The term "substantially" as used herein means the exclusion of a mode in which another component for expressing an effect other than an effect resulting from the polymer (I) is positively provided to the polymer (I) or positively used in combination with the polymer (I). For example, the incorporation of an impurity or the like inevitably mixed in due to a production process or the like is permitted to such an extent that the effect of the present invention is not impaired.

The polymer (I) contains 50 mol % to 100 mol % of the structural unit derived from an N-vinyl lactam-based monomer with respect to 100 mol % of the structural units derived from all monomers, and from the viewpoint that the effect of the present invention can be further expressed, contains preferably 60 mol % to 100 mol % thereof, more preferably from 70 mol % to 100 mol % thereof.

The polymer (I) may contain only one kind, or two or more kinds of structural units each derived from an N-vinyl lactam-based monomer. The N-vinyl lactam-based monomers may be used alone or in combination thereof.

A typical example of the structural unit derived from an N-vinyl lactam-based monomer is a structural unit represented by the general formula (1).

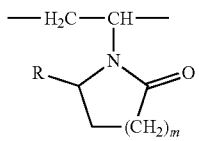

(1)

In the general formula (1), R represents a hydrogen atom or a methyl group.

In the general formula (1), "m" represents an integer of from 1 to 3.

Herein, a structural unit derived from a monomer is a structural unit having the same structure as that formed through polymerization of the monomer. However, the structural unit derived from a monomer is not limited to a structural unit actually formed through polymerization of the monomer, and the structural unit derived from a monomer encompasses any structural unit having the same structure as that formed through polymerization of the monomer.

A typical example of a monomer capable of forming the structural unit derived from an N-vinyl lactam-based monomer is an N-vinyl lactam-based monomer represented by the general formula (2).

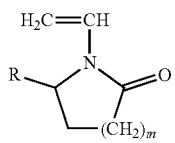

(2)

In the general formula (2), R represents a hydrogen atom or a methyl group.

In the general formula (2), "m" represents an integer of from 1 to 3.

Examples of the monomer represented by the general formula (2) include N-vinylpyrrolidone, N-vinylpiperidone, and N-vinylcaprolactam. From the viewpoint that the effect of the present invention can be further expressed, the monomer represented by the general formula (2) is preferably N-vinylpyrrolidone.

The polymer (I) may have another structural unit in addition to the structural unit derived from an N-vinyl lactam-based monomer. The other structural unit is a structural unit derived from another monomer different from the N-vinyl lactam-based monomer.

The other structural units may be used alone or in combination thereof. The other monomers may be used alone or in combination thereof.

Any appropriate monomer may be adopted as the other monomer as long as the monomer can be copolymerized with the N-vinyl lactam-based monomer to such an extent that the effect of the present invention is not impaired. Examples of such other monomer include:
1) (meth)acrylic acid esters, such as methyl (meth)acrylate, ethyl (meth)acrylate, butyl (meth)acrylate, and cyclohexyl (meth)acrylate;
2) hydroxyethyl (meth)acrylate, hydroxypropyl (meth)acrylate, 3-(meth)allyloxy-1,2-dihydroxypropane, (meth)allyl alcohol, isoprenol, and unsaturated alcohols each obtained by adding an alkylene oxide to a hydroxy group of any such compound;
3) (meth)acrylamide, and derivatives of (meth)acrylamide, such as N-monomethyl (meth)acrylamide, N-monoethyl (meth)acrylamide, and N,N-dimethyl (meth)acrylamide;
4) basic unsaturated monomers, such as dimethylaminoethyl (meth)acrylate, dimethylaminoethyl (meth)acrylamide, vinylpyridine, and vinylimidazole, and salts or quaternized products thereof;
5) vinylamides, such as vinylformamide, vinylacetamide, and vinyloxazolidone;
6) carboxyl group-containing unsaturated monomers, such as (meth)acrylic acid, itaconic acid, maleic acid, and fumaric acid, and salts thereof;
7) unsaturated anhydrides, such as maleic anhydride and itaconic anhydride;
8) vinyl esters, such as vinyl acetate and vinyl propionate;
9) vinylethylene carbonate and derivatives thereof;
10) styrene and derivatives thereof;
11) 2-sulfoethyl (meth)acrylate and derivatives thereof;
12) vinylsulfonic acids and derivatives thereof, such as 3-allyloxy-2-hydroxypropanesulfonic acid, (meth)allylsulfonic acid, isoprenesulfonic acid, and salts thereof;
13) vinyl ethers, such as methyl vinyl ether, ethyl vinyl ether, and butyl vinyl ether; and
14) olefins, such as ethylene, propylene, octene, and butadiene.

When the other monomer is the above-mentioned 2), the alkylene oxide is preferably an alkylene oxide having 1 to 20 carbon atoms, more preferably an alkylene oxide having 1 to 4 carbon atoms. From the viewpoint that the effect of the present invention can be further expressed, the alkylene oxide is preferably at least one kind selected from the group consisting of: ethylene oxide; and propylene oxide.

When the other monomer is the above-mentioned 2), the number of moles added of the alkylene oxide is preferably from 0 mol to 50 mol, more preferably from 0 mol to 20 mol per 1 mol of the compound of the above-mentioned 2).

From the viewpoint of, for example, copolymerizability with the N-vinyl lactam-based monomer, the other monomer is preferably one of 1) to 9) among the above-mentioned 1) to 14), more preferably one of 1) to 6).

From the viewpoint that the effect of the present invention can be further expressed, the content of the structural unit derived from the other monomer in the polymer (I) is preferably from 0 mol % to 50 mol %, more preferably from 0 mol % to 40 mol %, still more preferably from 0 mol % to 30 mol % with respect to 100 mol % of the structural units derived from all monomers.

The polymer (I) preferably has a crosslinked structure. When the polymer (I) has the crosslinked structure, the effect of the present invention can be further expressed.

The crosslinked structure is at least one kind selected from the group consisting of: a structure derived from a crosslinking agent having at least two polymerizable double bond groups per molecule; and a structure formed through a reaction between main chains or side chains of a polymer.

Any appropriate crosslinking agent may be adopted as the crosslinking agent to such an extent that the effect of the present invention is not impaired. Examples of such crosslinking agent include N,N'-methylenebis(meth)acrylamide, (poly)ethylene glycol di(meth)acrylate, (poly)propylene glycol di(meth)acrylate, trimethylolpropane tri(meth)acrylate, trimethylolpropane di(meth)acrylate, glycerin tri(meth)acrylate, glycerin acrylate methacrylate, ethylene oxide-modified trimethylolpropane tri(meth)acrylate, pentaerythritol tetra(meth)acrylate, pentaerythritol tri(meth)acrylate, dipentaerythritol hexa(meth)acrylate, triallyl cyanurate (cyanuric acid triallyl ester), triallyl isocyanurate, triallyl phosphate, triallylamine, pentaerythritol tetraallyl ether, pentaerythritol triallyl ether, pentaerythritol diallyl ether, poly(meth)allyloxyalkanes, divinylbenzene, divinyltoluene, divinylxylene, divinylnaphthalene, divinyl ether, divinyl ketone, trivinylbenzene, tolylene diisocyanate, hexamethylene diisocyanate, diallyl carbonate, 1,3-bis(allyloxy)-2-propanol, divinylethylene urea, 1,4-butylenebis(N-vinylamide), and (di, tri, tetra, penta, hexa, hepta, and octa)allyl sucroses.

Of the above-mentioned crosslinking agents, a compound having two or more allyl groups is preferably used because the amounts of a residual N-vinyl lactam-based monomer and a residual soluble component (which is an uncrosslinked polymer component and is a component dissolved in water) tend to be reduced. Specifically, pentaerythritol (di, tri, and tetra) (meth)allyl ethers, triallyl isocyanurate, triallyl phosphate, triallylamine, diallyl carbonate, 1,4-butylenebis(N-vinylamide), and (di, tri, tetra, penta, hexa, hepta, and octa)allyl sucroses are preferred, and pentaerythritol (di, tri, and tetra)allyl ethers and (di, tri, tetra, penta, hexa, hepta, and octa)allyl sucroses are more preferred. The pentaerythritol (di, tri, and tetra)allyl ethers and the (di, tri, tetra, penta, hexa, hepta, and octa)allyl sucroses each have higher safety, and hence a crosslinked polymer obtained by employing such crosslinking agent can be more suitably used for cosmetic applications.

The crosslinking agents may be used alone or in combination thereof.

When the polymer (I) has the crosslinked structure, from the viewpoint that the effect of the present invention can be further expressed, the content of a structural unit derived from the crosslinking agent in the polymer (I) is preferably from 0.001 mol % to 10 mol %, more preferably from 0.005 mol % to 5 mol %, still more preferably from 0.01 mol % to 5 mol %, particularly preferably from 0.01 mol % to 1 mol %, most preferably from 0.05 mol % to 0.8 mol % with respect to 100 mol % of the structural units derived from all monomers.

The crosslinking agent has polymerizable double bond groups. However, herein, the crosslinking agent is not regarded as a monomer for the purpose of clarification of composition. That is, the crosslinking agent is not included in the "all monomers".

The additive for a chemical agent may contain another polymer in addition to the polymer (I). From the viewpoint that the effect of the present invention can be further expressed, the content of such other polymer is preferably from 0 wt % to 50 wt %, more preferably from 0 wt % to 30 wt %, still more preferably from 0 wt % to 10 wt %, particularly preferably from 0 wt % to 5 wt %, most preferably substantially 0 wt % with respect to 100 wt % of the additive for a chemical agent.

The shape of the additive for a chemical agent is preferably particulate. That is, the additive for a chemical agent is preferably in the form of particles. Examples of the shape of each of the particles include a spherical shape, a cubic shape, a rectangular parallelepiped shape, and an indefinite shape.

The average particle diameter of the additive for a chemical agent in a state of having been dried under a reduced pressure of 0.02 MPa or less at 100° C. for 1 hour is 100 µm or less, preferably 80 µm or less, more preferably 60 µm or less, still more preferably 40 µm or less, particularly preferably 30 µm or less, most preferably 25 µm or less. The lower limit value of the average particle diameter in a state of having been dried under a reduced pressure of 0.02 MPa or less at 100° C. for 1 hour is practically 0.1 µm or more. By virtue of the average particle diameter falling within the above-mentioned ranges in a state of having been dried under a reduced pressure of 0.02 MPa or less at 100° C. for 1 hour, the additive for a chemical agent can improve the functions of various chemical agents. Any dryer and pressure reducing device may be used as means for the drying under a reduced pressure of 0.02 MPa or less at 100° C. for 1 hour as long as the means provides conditions that enable the drying under a reduced pressure of 0.02 MPa or less at 100° C. for 1 hour.

The average particle diameter of the additive for a chemical agent in a state of having been dried under a reduced pressure of 0.02 MPa or less at 100° C. for 1 hour is typically a 50% cumulative value of a volume distribution measured with a laser diffraction particle size distribution measurement apparatus (dry). Examples of the laser diffraction particle size distribution measurement apparatus (dry) include a product of the Mastersizer 3000 model manufactured by the Malvern division of Spectris Co., Ltd. and a product of the Partica LA-950V2 model manufactured by Horiba, Ltd. Specifically, the average particle diameter may be determined by a method described in Examples to be described later.

When the additive for a chemical agent is blended into a cosmetic or the like, the additive for a chemical agent is brought into a form swelled with a medium, such as water. The average particle diameter of such swelled body of the additive for a chemical agent is preferably 180 µm or less, more preferably 100 µm or less in terms of average particle diameter of a swelled body obtained by swelling the additive for a chemical agent with deionized water. The lower limit value of the average particle diameter of the swelled body obtained by swelling the additive for a chemical agent with deionized water is practically 0.1 µm or more. When the average particle diameter of the swelled body obtained by swelling the additive for a chemical agent with deionized water falls within the above-mentioned ranges, the additive for a chemical agent can become capable of further improving the functions of various chemical agents.

The average particle diameter of the swelled body obtained by swelling the additive for a chemical agent with deionized water is typically a 50% cumulative value of a volume distribution measured with a laser diffraction particle size distribution measurement apparatus (wet). Examples of the laser diffraction particle size distribution measurement apparatus (wet) include a product of the Mastersizer 3000 model manufactured by the Malvern division of Spectris Co., Ltd. and a product of the Partica LA-950V2 model manufactured by Horiba, Ltd. Specifically, the average particle diameter may be determined by a method described in Examples to be described later.

The additive for a chemical agent may contain any appropriate other component in addition to the polymer (I) and the other polymer that may be incorporated as required, to such an extent that the effect of the present invention is not impaired. From the viewpoint that the effect of the present invention can be further expressed, the content of such other component is preferably from 0 wt % to 10 wt %, more preferably from 0 wt % to 5 wt %, still more preferably from 0 wt % to 3 wt %, particularly preferably from 0 wt % to 1 wt %, most preferably substantially 0 wt % with respect to 100 wt % of the additive for a chemical agent.

<<Production Method for Additive for a Chemical Agent>>

The additive for a chemical agent according to the embodiment of the present invention may be produced by any appropriate method to such an extent that the effect of the present invention is not impaired. Such production method preferably includes a step of subjecting a monomer component serving as at least one kind of raw material for forming the polymer (I) to a polymerization reaction.

The monomer component for forming the polymer (I) contains mol % to 100 mol %, preferably 60 mol % to 100 mol %, more preferably 70 mol % to 100 mol % of an N-vinyl lactam-based monomer with respect to 100 mol % of the entire monomer component.

The N-vinyl lactam-based monomers may be used alone or in combination thereof.

For the details of the N-vinyl lactam-based monomer, the description in the section <<Additive for a Chemical Agent>> may be cited as it is.

The monomer component may contain another monomer in addition to the N-vinyl lactam-based monomer. The other monomers may be used alone or in combination thereof.

From the viewpoint that the effect of the present invention can be further expressed, the monomer component contains preferably 0 mol % to 50 mol %, more preferably 0 mol % to 40 mol %, still more preferably 0 mol % to 30 mol % of the other monomer with respect to 100 mol % of the entire monomer component.

For the details of the other monomer, the description in the section <<Additive for a Chemical Agent>> may be cited as it is.

The polymer (I) preferably has a crosslinked structure from the viewpoint that the effect of the present invention can be further expressed. The crosslinked structure is at least one kind selected from the group consisting of: a structure derived from a crosslinking agent having at least two polymerizable double bond groups per molecule; and a structure formed through a reaction between main chains or side chains of a polymer, and may be constructed by at least one kind selected from the group consisting of: use of a crosslinking agent in the step of subjecting the monomer component to a polymerization reaction; and crosslinking treatment of a polymer.

When the crosslinking agent is used, from the viewpoint that the effect of the present invention can be further expressed, the use amount of the crosslinking agent is preferably from 0.001 mol % to 10 mol %, more preferably from 0.005 mol % to 5 mol %, still more preferably from 0.01 mol % to 5 mol %, particularly preferably from 0.01 mol % to 1 mol %, most preferably from 0.05 mol % to 0.8 mol % with respect to 100 mol % of the entire monomer component.

For the details of the crosslinking agent, the description in the section <<Additive for a Chemical Agent>> may be cited as it is.

As described above, the method of producing the polymer (I) preferably includes the step of subjecting a monomer component serving as at least one kind of raw material for forming the polymer (I) to a polymerization reaction. Any appropriate polymerization method may be adopted as a method for such polymerization reaction to such an extent that the effect of the present invention is not impaired. Examples of such polymerization method include a bulk polymerization method, a solution polymerization method, an emulsion polymerization method, a suspension polymerization method, and a precipitation polymerization method. Of those polymerization methods, from the viewpoint that the effect of the present invention can be further expressed, a solution polymerization method or a precipitation polymerization method is preferred, and a precipitation polymerization method is more preferred.

<Production Method Using Precipitation Polymerization Method>

The precipitation polymerization method typically includes a dropping step of separately dropping a monomer component containing the N-vinyl lactam-based monomer, and a polymerization initiator into a reaction medium.

The amount of the polymerization initiator in the initial reaction medium before the dropping step is preferably 30 wt % or less, more preferably 20 wt % or less, still more preferably 10 wt % or less, particularly preferably from 0 wt % to 5 wt % with respect to the whole amount of the polymerization initiator to be used for the reaction.

In the dropping step, it is preferred that: the polymerization initiator be dropped over a period of time longer than the dropping time of the monomer component; and a polymer be obtained as aggregates. The aggregates preferably include spherical objects, and examples of the spherical objects include perfectly spherical objects, approximately spherical objects, and objects each having an approximately elliptic shape in plan view.

The "precipitation polymerization method" is a polymerization method in such a polymerization system that the monomer component is compatible with/dissolved in a polymerization solvent, but a produced polymer does not dissolve in the polymerization solvent. In this polymerization method, the produced polymer is deposited (precipitated) along with the progress of the polymerization reaction. The deposited polymer is swelled with the monomer component, and the polymerization reaction progresses in each of the solvent and the vicinity of the polymer. In this case, a polymerization initiator is used, and such polymerization initiator is preferably soluble in both of the polymerization solvent and the monomer component.

In the dropping step, as a method for the separate dropping of the monomer component containing the N-vinyl lactam-based monomer, and the polymerization initiator into the reaction medium, for example, it is appropriate to place the monomer component containing the N-vinyl lactam-based monomer, and the polymerization initiator in different dropping funnels, and to separately drop the monomer component containing the N-vinyl lactam-based monomer, and the polymerization initiator into a reaction vessel having placed therein the initial reaction medium. The monomer component containing the N-vinyl lactam-based monomer, and the polymerization initiator may each be a mixed solution with a solvent.

In the precipitation polymerization method, a solvent is used as the reaction medium. Examples of the solvent include hydrocarbon-based solvents, such as heptane and cyclohexane.

Examples of the initial reaction medium before the dropping step include a solvent, and a solvent having added thereto the polymerization initiator within the above-mentioned ranges. The amount of the monomer component in the initial reaction medium is preferably 30 wt % or less, more preferably 20 wt % or less, still more preferably 10 wt % or less, particularly preferably from 0 wt % to 5 wt % with respect to the whole amount of the monomer component.

The dropping time of the monomer component into the initial reaction medium is preferably from 0.5 hour to 10.0 hours. In addition, the dropping time of the polymerization initiator into the initial reaction medium is preferably longer than the dropping time of the monomer component, more preferably from 1.0 hour to 20 hours. The dropping time of the polymerization initiator into the initial reaction medium is preferably from 1.10 times to 3.00 times, more preferably from 1.15 times to 2.50 times, still more preferably from 1.20 times to 2.00 times as long as the dropping time of the monomer component.

When the precipitation polymerization method is performed, a polymerization temperature is preferably +15° C. or more and +30° C. or less with respect to the 10-hour half-life temperature of the polymerization initiator. The polymerization temperature refers to the temperature of the reaction liquid during the dropping of the monomer component. When the temperature fluctuates during the reaction, the polymerization temperature refers to a median value between the maximum temperature and the lowest temperature. The "10-hour half-life temperature" refers to a temperature at which the concentration of the polymerization initiator becomes ½ of the initial value after 10 hours from the initiation of the reaction, and is generally used as a criterion for selecting a polymerization initiator.

When the polymerization initiator is added in one portion at the initial stage, an initiating radical concentration in the reaction system reduces with the passage of time. However, when the polymerization initiator is dropped into a reaction liquid having an appropriate temperature, the initiating radical concentration is kept constant to stabilize monomer consumption, with the result that the agglomeration of a polymerized product and the adhesion thereof to a vessel wall or a stirring blade can be suppressed. The polymerization initiator is described later.

For example, a value published by a manufacturer may be used as the 10-hour half-life temperature of the polymerization initiator. The 10-hour half-life temperatures of organic peroxide-based initiators, which are published by, for example, NOF Corporation, are as follows: 32.7° C. for isobutyl peroxide; 36.5° C. for cumyl peroxyneodecanoate; 40.3° C. for di-n-propyl peroxydicarbonate; 40.5° C. for diisopropyl peroxydicarbonate; 40.5° C. for di-sec-butyl peroxydicarbonate; 40.7° C. for 1,1,3,3-tetramethylbutyl peroxyneodecanoate; 40.8° C. for di(4-t-butylcyclohexyl) peroxydicarbonate; 43.6° C. for di(2-ethylhexyl) peroxydicarbonate; 44.5° C. for t-hexyl peroxyneodecanoate, 46.4° C. for t-butyl peroxyneodecanoate; 53.2° C. for t-hexyl peroxypivalate; 54.6° C. for t-butyl peroxypivalate; 59.4° C. for di(3,5,5-trimethylhexanoyl) peroxide; 61.6° C. for dilauroyl peroxide; 65.3° C. for 1,1,3,3-tetramethylbutyl peroxy-2-ethylhexanoate; 65.9° C. for disuccinic acid peroxide; 66.2° C. for 2,5-dimethyl-2,5-di(2-ethylhexanoylperoxy)hexane; 69.9° C. for t-hexyl peroxy-2-ethylhexanoate; 72.1° C. for t-butyl peroxy-2-ethylhexanoate; 73.1° C. for a mixture of di(3-methylbenzoyl) peroxide, benzoyl(3-methylbenzoyl) peroxide, and dibenzoyl peroxide; 73.6° C. for dibenzoyl peroxide; 87.1° C. for 1,1-di(t-hexylperoxy)cyclohexane; 90.7° C. for 1,1-di(t-butylperoxy)cyclohexane; 94.7° C. for 2,2-di(4,4-di-(t-butylperoxy)cyclohexyl)propane; 95.0° C. for t-hexyl peroxyisopropyl monocarbonate; 97.1° C. for t-butyl peroxy-3,5,5-trimethylhexanoate; 98.3° C. for t-butyl peroxylaurate; 98.7° C. for t-butyl peroxyisopropyl monocarbonate; 99.0° C. for t-butyl peroxy-2-ethylhexyl monocarbonate; 99.4° C. for t-hexyl peroxybenzoate; 99.7° C. for 2,5-dimethyl-2,5-di(benzoylperoxy)hexane; 101.9° C. for t-butyl peroxyacetate; 103.1° C. for 2,2-di(t-butylperoxy)butane; 104.3° C. for t-butyl peroxybenzoate; 104.5° C. for n-butyl 4,4,-di(t-butylperoxy)valerate; 119.2° C. for di(2-t-butylperoxyisopropyl)benzene; 116.4° C. for dicumyl peroxide; 116.4° C. for di-t-hexyl peroxide; 117.9° C. for 2,5-dimethyl-2,5-di(t-butylperoxy)hexane; 119.5° C. for t-butylcumyl peroxide; has 123.7° C. for di-t-butyl peroxide; 128.0° C. for p-menthane hydroperoxide; 128.4° C. for 2,5-dimethyl-2,5-di(t-butylperoxy)hexyne-3; 145.1° C. for diisopropylbenzene; 152.9° C. for 1,1,3,3-tetramethylbutyl hydroperoxide; 157.9° C. for cumene hydroperoxide; and 166.5° C. for t-butyl hydroperoxide. In addition, there is also a disclosure from Arkema Yoshitomi, Ltd. of the 10-hour half-life temperatures of similar polymerization initiators.

The 10-hour half-life temperatures of azo-based polymerization initiators, which are published by, for example, FUJIFILM Wako Pure Chemical Corporation, are as follows: 65° C. for 2,2-azobis(isobutyronitrile); 30° C. for 2,2'-azobis(4-methoxy-2,4-dimethylvaleronitrile); 51° C. for 2,2'-azobis(2,4-dimethylvaleronitrile); 66° C. for dimethyl 2,2'-azobis(2-methylpropionate); 67° C. for 2,2'-azobis(2-methylbutyronitrile); 88° C. for 1,1'-azobis(cyclohexane-1-carbonitrile); 110° C. for 2,2'-azobis(N-butyl-2-methylpropionamide); and 73° C. for dimethyl 1,1-azobis(1-cyclohexanecarboxylate).

In the precipitation polymerization method, any appropriate polymerization initiator may be adopted as the polymerization initiator to such an extent that the effect of the present invention is not impaired. Examples of such polymerization initiator include a persulfate, hydrogen peroxide, an organic peroxide, and an azo compound. Of those, an organic peroxide and an azo compound are preferred. A redox-type initiator for generating a radical by combining an oxidant and a reductant may also be used as the polymerization initiator. The polymerization initiators may be used alone or in combination thereof.

Examples of the organic peroxide include diisobutyl peroxide, cumyl peroxyneodecanoate, di-n-propyl peroxydicarbonate, diisopropyl peroxydicarbonate, di-sec-butyl peroxydicarbonate, 1,1,3,3-tetramethylbutyl peroxyneodecanoate, di(4-t-butylcyclohexyl)peroxydicarbonate, di(2-ethylhexyl)peroxydicarbonate, t-hexyl peroxyneodecanoate, t-butyl peroxyneodecanoate, t-hexyl peroxypivalate, t-butyl peroxypivalate, di(3,5,5-trimethylhexanoyl) peroxide, dilauroyl peroxide, 1,1,3,3-tetramethylbutyl peroxy-2-ethylhexanoate, disuccinic acid peroxide, 2,5-dimethyl-2,5-di(2-ethylhexanoylperoxy) hexane, t-hexyl peroxy-2-ethylhexanoate, t-butyl peroxy-2-ethylhexanoate, a mixture of di(3-methylbenzoyl) peroxide, benzoyl(3-methylbenzoyl) peroxide, and dibenzoyl peroxide, dibenzoyl peroxide, 1,1-di(t-hexylperoxy)cyclohexane, 1,1-di(t-butylperoxy)cyclohexane, 2,2-di(4,4-di-(t-butylperoxy)cyclohexyl)propane, t-hexyl peroxyisopropyl monocarbonate, t-butyl peroxy-3,5,5-trimethylhexanoate, t-butyl peroxylaurate, t-butyl peroxyisopropyl monocarbonate, t-butyl peroxy-2-ethylhexyl monocarbonate, t-hexyl peroxybenzoate, 2,5-dimethyl-2,5-di(benzoylperoxy)hexane, t-butyl peroxyacetate, 2,2-di(t-butylperoxy)butane, t-butyl peroxybenzoate, n-butyl-4,4,-di(t-butylperoxy)valerate, di(2-t-butylperoxyisopropyl) benzene, dicumyl peroxide, di-t-hexyl peroxide, 2,5-dimethyl-2,5-di(t-butylperoxy)hexane, t-butylcumyl peroxide, di-t-butyl peroxide, p-menthane hydroperoxide, 2,5-dimethyl-2,5-di(t-butylperoxy)hexyne-3, diisopropylbenzene, 1,1,3,3-tetramethylbutyl hydroperoxide, cumene hydroperoxide, and t-butyl hydroperoxide.

Examples of the azo compound include 2,2-azobis(isobutyronitrile), 2,2'-azobis(4-methoxy-2,4-dimethylvaleronitrile), 2,2'-azobis(2,4-dimethylvaleronitrile), dimethyl-2,2'-azobis(2-methylpropionate), 2,2'-azobis(2-methylbutyronitrile), 1,1'-azobis(cyclohexane-1-carbonitrile), 2,2'-azobis(N-butyl-2-methylpropionamide), and dimethyl-1,1-azobis(1-cyclohexanecarboxylate).

The use amount of the polymerization initiator is preferably from 0.01 g to 10 g, more preferably from 0.05 g to 7 g, still more preferably from 0.1 g to 5 g with respect to 1 mol of the total amount of all monomers and the crosslinking agent. When the use amount of the polymerization initiator is set as just described, the ratios of an unreacted monomer and crosslinking agent contained in the polymer to be obtained can be sufficiently reduced.

A reaction vessel of any appropriate material may be adopted as a reaction vessel in which the polymerization step is performed as long as the polymerization step can be performed therein. An example of such reaction vessel is a reaction vessel of a material such as stainless steel. When the polymerization reaction is performed using the reaction vessel of such material capable of easily transferring heat, the polymerization reaction sufficiently progresses, and hence the contents of the unreacted monomer and crosslinking agent in the polymer to be obtained can be reduced. In addition, it is also preferred to use a reaction vessel of a material free of iron leaching, such as polypropylene, and the use of the reaction vessel of such material can reduce the content of iron in the polymer to be obtained.

Any appropriate shape may be adopted as the shape of a stirring blade in performing the polymerization reaction in the polymerization step to such an extent that the effect of the present invention is not impaired. Examples of such shape include a paddle type, a multi-stage paddle type, an inclined paddle type, an anchor type, a propeller type, a combination thereof, and a Maxblend type.

When the polymerization is performed by the precipitation polymerization method, the polymerization can be easily controlled. According to the precipitation polymerization method, a polymer containing spherical objects in each of which extremely small primary particles are loosely aggregated is obtained in a preferred manner. The spherical objects are easy to handle because of their self-weights outweighing the influences of static electricity and a flow of air, making it difficult for the powder to be scattered, and besides, can be extremely easily pulverized. Accordingly, an excellent effect of requiring no special pulverizer for pulverization can be expressed. In addition, the aggregated spherical objects as described above are quickly dispersed into primary particles when put into a solution, and hence can provide a uniform dispersion or gel-like substance within a short period of time. Similarly, spherical objects after pulverization are also quickly dispersed into primary particles when put into a solution, and hence can provide a uniform dispersion or gel-like substance within a short period of time.

The polymer obtained by the precipitation polymerization method is preferably spherical objects of several hundred μm. The size of each of such spherical objects is preferably from more than 100 μm to 2,000 μm, more preferably from 200 μm to 1,500 μm, still more preferably from 300 μm to 1,000 μm.

The polymer obtained by the precipitation polymerization method, which is preferably spherical objects, is an aggregate of indefinite-shaped primary particles, and the particle diameter of each of such indefinite-shaped primary particles is preferably 2 μm or less, more preferably from 10 nm to 2,000 nm, still more preferably from 20 nm to 1,000 nm.

The precipitation polymerization method may include any appropriate other step in addition to the polymerization step to such an extent that the effect of the present invention is not impaired. Examples of such other step include a drying step, a pulverization step, a classification step, a granulation step, and a post-crosslinking step.

The precipitation polymerization method preferably includes a drying step. The "drying" refers to an operation of increasing a solid content, and in general, the ratio of the solid content to the weight of the whole polymer only needs to be increased as compared to that before the drying. The drying may be performed simultaneously with part of the polymerization, and drying during the polymerization and drying after the polymerization may be used in combination. It is preferred that a drying step of performing drying with a dryer be provided after the polymerization.

The drying step is performed so as to fall within the range of from 80° C. to 250° C. preferably for a period of time that is 50% or more of the total time of the drying step, or preferably substantially throughout the entire drying step. When the drying step is performed in this manner, various physical properties of the polymer can be further improved. The drying temperature is defined by a heat medium temperature. However, in the case where the drying temperature cannot be defined by the heat medium temperature, such as the case of a microwave, the drying temperature is defined by a material temperature. Any appropriate drying method may be adopted as a method for the drying as long as the drying temperature falls within the above-mentioned range to such an extent that the effect of the present invention is not impaired. Examples of such drying method include hot-air drying, windless drying, drying under reduced pressure, infrared drying, and microwave drying. Of those drying methods, hot-air drying or drying under reduced pressure is preferably used. When the hot-air drying is used, the flow rate of drying air is preferably from 0.01 m/sec to 10 m/sec, more preferably from 0.1 m/sec to 5 m/sec. The range of the drying temperature is more preferably from 110° C. to 220° C., still more preferably from 120° C. to 200° C. In addition, the drying may be performed at a constant temperature, or the drying may be performed at varying temperatures, but it is preferred that substantially the entire drying step be performed in the above-mentioned temperature range.

From the viewpoint that the effect of the present invention can be further expressed, the precipitation polymerization method preferably includes a pulverization step. The pulverization step is preferably performed using a pulverizer. When the precipitation polymerization method includes the drying step, the pulverization step may be performed before, during, or after the drying step, and is preferably performed after the drying step.

As described above, according to the precipitation polymerization method, a polymer containing spherical objects in each of which extremely small primary particles are loosely aggregated is obtained in a preferred manner, and can be extremely easily pulverized, and hence an excellent effect of requiring no special pulverizer for the pulverization can be expressed. Accordingly, a simple pulverizer can be adopted as the pulverizer. Examples of such pulverizer include a roll-type pulverizer, such as a roll mill, a hammer-type pulverizer, such as a hammer mill, an impact-type pulverizer, a cutter mill, a turbo grinder, a ball mill, a flash mill, and a jet mill. Of those, a roll mill is preferably used when particle size distribution is to be further controlled. In order to control the particle size distribution, two or more times of pulverization may be performed in succession, or three or more times of pulverization may be performed in succession. In addition, in the case of performing two or more times of pulverization, respective pulverizers may be the same as or different from each other. In addition, different kinds of pulverizers may be used in combination.

In order that the polymer to be obtained by the precipitation polymerization method may be controlled to have a specific particle size distribution, a classification step or a granulation step may be provided. In the classification step, a sieve having a specific aperture may be used. Any appropriate classifier may be adopted as a classifier to be used for performing classification with the sieve to such an extent that the effect of the present invention is not impaired. Examples of such classifier include a vibration sieve (e.g., unbalanced weight-driven type, resonant type, vibrating motor type, electromagnetic type, or circular vibration type), an in-plane motion sieve (e.g., horizontal motion type, horizontal circle-linear motion type, or three-dimensional circle motion type), a movable net sieve, a compulsory stirring sieve, a net plane vibration sieve, a wind force sieve, and a sonic sieve.

<Production Method Using Solution Polymerization Method>

In the solution polymerization method, a solvent is preferably used. An example of the solvent is at least one kind selected from the group consisting of: water; and an alcohol. Examples of the alcohol include methyl alcohol, ethyl alcohol, isopropyl alcohol, n-butyl alcohol, and diethylene glycol. When the solvent is used, the concentration of the monomer component in the solution is preferably 20 wt % or more and 80 wt % or less. When the concentration of the monomer component in the solution is less than 20 wt %, there is a risk in that the polymer may be difficult to obtain, or even when obtained, may be difficult to disintegrate after the polymerization. In addition, drying after the polymerization reaction requires a long period of time, and hence there is a risk in that the polymer may be deteriorated during the drying. Meanwhile, when the concentration of the monomer component in the solution is more than 80 wt %, the polymerization becomes difficult to control, and hence there is a risk in that the residual monomer may be increased.

In the solution polymerization method, any appropriate conditions may be adopted as reaction conditions, such as a reaction temperature and a pressure, in the polymerization reaction to such an extent that the effect of the present invention is not impaired. As such conditions, for example, the reaction temperature is preferably set to from 20° C. to 150° C., and the pressure in the reaction system is preferably set to normal pressure or reduced pressure.

In the solution polymerization method, any appropriate means may be adopted as means for initiating the polymerization of the monomer component to such an extent that the effect of the present invention is not impaired. Examples of such means include a method involving adding a polymerization initiator, a method involving performing UV irradiation, a method involving applying heat, and a method involving performing light irradiation in the presence of a photoinitiator.

Any appropriate polymerization initiator may be adopted as the polymerization initiator to such an extent that the effect of the present invention is not impaired. Examples of such polymerization initiator include: peroxides, such as hydrogen peroxide and t-butyl hydroperoxide; azo compounds, such as 2-(carbamoylazo)isobutyronitrile, 2,2'-azobis(2-amidinopropane) dihydrochloride, 2,2'-azobis(2-methyl-N-phenylpropionamidine) dihydrochloride, 2,2'-azobis[2-(N-allylamidino)propane] dihydrochloride, 2,2'-azobis[2-(5-hydroxy-3,4,5,6-tetrahydropyrimidin-2-yl) propane] dihydrochloride, 2,2'-azobis[2-(2-imidazolin-2-yl) propane], 2,2'-azobis[2-(2-imidazolin-2-yl)propane] dihydrochloride, 2,2'-azobis[2-(2-imidazolin-2-yl)propane] disulfate hydrate, 4,4'-azobis(4-cyanopentanoic acid), 2,2'-azobis[N-(2-carboxyethyl)-2-methylpropionamidine] n-hydrate, and 2,2'-azobis[2-methyl-N-(2-hydroxyethyl) propionamide]; persulfates, such as potassium persulfate, ammonium persulfate, and sodium persulfate; and redox-type initiators for generating radicals by combining oxidants and reductants, such as: ascorbic acid and hydrogen peroxide; sodium sulfoxylate and t-butyl hydroperoxide; and a persulfate and a metal salt. The polymerization initiators may be used alone or in combination thereof.

Any appropriate use amount may be adopted as the use amount of the polymerization initiator to such an extent that the effect of the present invention is not impaired. Such use amount is, for example, preferably from 0.002 wt % to 15 wt %, more preferably from 0.01 wt % to 5 wt % with respect to 100 wt % in total of all monomers (total of the N-vinyl lactam-based monomer and the other monomer) and the crosslinking agent.

In the solution polymerization method, a basic pH regulator may be used for the purposes of, for example, promoting the polymerization reaction and preventing the N-vinyl lactam-based monomer from being hydrolyzed. The addition of the basic pH regulator may be performed by any appropriate method to such an extent that the effect of the present invention is not impaired. For example, the basic pH regulator may be loaded into the system at the initial stage of the polymerization, or may be sequentially added during the polymerization. Specific examples of the basic pH regulator include: ammonia; aliphatic amines, such as monoethanolamine, diethanolamine, and triethanolamine; aromatic amines, such as aniline; and alkali metal hydroxides, such as sodium hydroxide and potassium hydroxide. Of those, ammonia, monoethanolamine, diethanolamine, sodium hydroxide, and potassium hydroxide are preferred. The basic pH regulators may be used alone or in combination thereof. When the basic pH regulator is used, any appropriate use amount may be adopted as its use amount to such an extent that the effect of the present invention is not impaired. With regard to such use amount, it is appropriate to use the basic pH regulator so that the solution during the polymerization falls within preferably the pH range of from 5 to 10, more preferably the pH range of from 7 to 9.

In the solution polymerization method, a transition metal salt may be used for the purpose of, for example, promoting the polymerization reaction. Specific examples of the transition metal salt include carboxylic acid salts and chlorides of copper, iron, cobalt, nickel, and the like. The transition metal salts may be used alone or in combination thereof. When the transition metal salt is used, any appropriate use amount may be adopted as its use amount to such an extent that the effect of the present invention is not impaired. Such use amount is preferably from 0.1 ppb to 20,000 ppb, more preferably from 1 ppb to 5,000 ppb in terms of weight ratio with respect to the monomer component.

In the solution polymerization method, any appropriate other additive may be used to such an extent that the effect of the present invention is not impaired. Examples of such other additive include a chain transfer agent and a buffer.

When the crosslinking agent is used in the solution polymerization method, a crosslinked polymer may be obtained by a method involving polymerizing the monomer component in the presence of the crosslinking agent, or a crosslinked polymer may be obtained by a method involving performing crosslinking treatment after the polymerization of the monomer component. It is preferred that a crosslinked polymer be obtained by a method involving polymerizing the monomer component in the presence of the crosslinking agent. Examples of the method involving performing crosslinking treatment after the polymerization include: (i) a method involving irradiating the polymer with UV, a γ ray, or an electron beam; (ii) a method involving applying heat to the polymer to cause self-crosslinking; (iii) a method involving incorporating a radical generator into the polymer, and then applying heat to cause self-crosslinking; and (iv) a method involving incorporating a radically polymerizable crosslinking agent and a radical polymerization initiator into the polymer, followed by heating and/or light irradiation.

In the solution polymerization method, any appropriate addition method may be adopted as a method of adding each component to be loaded, to such an extent that the effect of the present invention is not impaired. Examples of such addition method include a batch system and a continuous system.

When the N-vinyl lactam-based monomer is used as the monomer component in the solution polymerization method, the method preferably includes, after the polymerization reaction, a step of adding an organic acid to the resultant polymer. When the organic acid is added to the resultant polymer, the amount of the residual N-vinyl lactam-based monomer in the polymer can be reduced. Any appropriate organic acid may be adopted as such organic acid to such an extent that the effect of the present invention is not impaired. Examples of such organic acid include organic compounds each having an acid group, such as a carboxyl group, a sulfonic acid group, a phosphonic acid group, a sulfuric acid group, or a phosphoric acid group. Examples of such organic acid include malonic acid, oxalic acid, succinic acid, aspartic acid, citric acid, glutamic acid, fumaric acid, malic acid, maleic acid, phthalic acid, trimellitic acid, pyromellitic acid, propionic acid, heptanoic acid, octanoic acid, glycolic acid, salicylic acid, lactic acid, L-ascorbic acid, benzoic acid, methanesulfonic acid, benzenesulfonic acid, laurylbenzenesulfonic acid, p-toluenesulfonic acid, benzenephosphonic acid, and laurylsulfuric acid. The organic acids may be used alone or in combination thereof.

Any appropriate use amount may be adopted as the use amount of the organic acid to such an extent that the effect of the present invention is not impaired. Such use amount is, for example, preferably from 0.01 wt % to 5 wt %, more preferably from 0.05 wt % to 3 wt %, still more preferably from 0.1 wt % to 1 wt % with respect to 100 wt % of the N-vinyl lactam-based monomer loaded in the reaction step. When the use amount of the organic acid falls within the above-mentioned ranges, the amount of the organic acid (salt) can also be reduced while the amount of the residual N-vinyl lactam-based monomer in the polymer to be obtained is reduced. The organic acid (salt) refers to the organic acid and/or a salt of the organic acid, and the salt of the organic acid is mainly a neutralization product of a base added in a neutralization step to be described later and the organic acid.

Any appropriate reaction time may be adopted as the reaction time of the organic acid and the polymer to such an extent that the effect of the present invention is not impaired. Such reaction time is preferably from 10 minutes to 3 hours, more preferably from 30 minutes to 2 hours. In the case where the polymer is a crosslinked polymer, it takes a longer period of time for the organic acid to penetrate into the polymer than in the case of an uncrosslinked polymer. However, when the reaction time of the organic acid and the polymer is 10 minutes or more, the organic acid more sufficiently penetrates into the polymer, and hence the amount of the residual N-vinyl lactam-based monomer in the polymer to be obtained can be more sufficiently reduced. In addition, from the viewpoint of productivity, the reaction time of the organic acid and the polymer is preferably set to 3 hours or less.

The solution polymerization method preferably includes a step of aging the polymer (aging step) after the polymerization reaction. Any appropriate temperature may be adopted as the temperature in the aging step to such an extent that the effect of the present invention is not impaired. Such temperature is preferably from 70° C. to 150° C., more preferably from 80° C. to 100° C. When the aging temperature falls within the above-mentioned ranges, the polymerization of the residual N-vinyl lactam-based monomer can be promoted.

In the solution polymerization method, any appropriate aging time may be adopted as the aging time in the aging step to such an extent that the effect of the present invention is not impaired. Such aging time is preferably from 10 minutes to 5 hours, more preferably from 30 minutes to 3 hours.

When the solution polymerization method includes the step of adding an organic acid, the aging step is preferably performed before the step of adding an organic acid.

In the solution polymerization method, the aging step is preferably performed while the polymer is disintegrated. When the solution polymerization method includes the step of adding an organic acid, the disintegration allows the organic acid to more sufficiently penetrate into the polymer, and hence the amount of the residual N-vinyl lactam-based monomer in the polymer to be obtained can be more sufficiently reduced. The disintegration of the polymer may be performed by a generally used method, and an example thereof is a disintegration method involving using a kneader.

When the organic acid is added in the solution polymerization method, the method preferably includes a neutralization step after the step of adding an organic acid. As a method for the neutralization, it is preferred to add a base after the organic acid has been allowed to react with the polymer. Examples of such base include: ammonia; aliphatic amines, such as monoethanolamine, diethanolamine, and triethanolamine; aromatic amines, such as aniline; and alkali metal hydroxides, such as sodium hydroxide and potassium hydroxide. Of those bases, ammonia, aliphatic amines, and alkali metal hydroxides are preferred, and ammonia, monoethanolamine, diethanolamine, sodium hydroxide, and potassium hydroxide are more preferred. Such bases may be used alone or in combination thereof.

The solution polymerization method may include another step. Examples of the other step include a drying step, a pulverization step, a classification step, and a granulation step.

In the drying step, the "drying" refers to an operation of increasing a solid content. In general, the solid content only needs to be increased as compared to that before the drying, and the solid content is increased to preferably 95 wt % or more, more preferably 96 wt % or more. The upper limit of the solid content is ideally 100 wt %, and is practically preferably 99 wt %. The drying and the polymerization may be simultaneously performed, and drying during the polymerization and drying after the polymerization may be used in combination. It is preferred that a drying step of performing drying with a dryer be performed after the polymerization. When the solution polymerization method includes the step of adding an organic acid, the drying step is preferably performed after the step of adding an organic acid. The solid content of the polymer refers to a value measured by a method described in Examples.

The temperature of the drying step is preferably set to be from 80° C. to 250° C. for a period of time that is 50% or more of the total time of the drying step, and is more preferably set to be from 80° C. to 250° C. for a period of time that is substantially 100% of the total time of the drying step. The range of the drying temperature is preferably from 80° C. to 250° C., more preferably from 110° C. to 220° C., still more preferably from 120° C. to 200° C. In addition, the drying may be performed at a constant temperature, or the drying may be performed at varying temperatures. When the temperature of the drying step is set as described above, various physical properties of the polymer can be further improved. The drying temperature may be defined by a heat medium temperature, and when the drying temperature cannot be defined by the heat medium temperature, the drying temperature may be defined by a material temperature.

Examples of the drying methods in the drying step include hot-air drying, windless drying, drying under reduced pressure, infrared drying, and microwave drying. Of those, hot-air drying is more preferably used. When the hot-air drying is used, the flow rate of drying air is preferably from 0.01 m/sec to 10 m/sec, more preferably from 0.1 m/sec to 5 m/sec.

In the pulverization step, a pulverizer is preferably used. When the solution polymerization method includes the drying step, the pulverization step may be performed before, during, or after the drying step. The pulverization step is preferably performed after the drying step.

For the pulverizer, the description in the section <Precipitation Polymerization Method> may be cited as it is.

For the classification step or the granulation step, the description in the section <Precipitation Polymerization Method> may be cited as it is.

<<Composition Containing an Additive for a Chemical Agent>>

The additive for a chemical agent according to the embodiment of the present invention may be combined with a chemical agent to provide a composition containing an additive for a chemical agent. That is, the composition containing an additive for a chemical agent contains the chemical agent and the additive for a chemical agent.

Any appropriate chemical agent may be adopted as the chemical agent to such an extent that the effect of the present invention is not impaired. Examples of such chemical agent include a cosmetic, a fragrance, an aromatic, a deodorant, a pharmaceutical, an insect repellent, an insecticide, and an agricultural chemical, and a typical example is a cosmetic.

The additive for a chemical agent according to the embodiment of the present invention expresses a function-improving effect on various chemical agents. Examples of such function-improving effect include the continuity of an effect and the improvement of an effect.

Any appropriate chemical agent may be adopted as the chemical agent to such an extent that the effect of the present invention is not impaired. Examples of such chemical agent include a UV absorber, an antioxidant, an antiseptic/antibacterial agent, and a fragrance.

Examples of the UV absorber include homomenthyl salicylate, 2-cyano-3,3-diphenylprop-2-enoic acid 2-ethylhexyl ester (also known as octocrylene), glyceryl mono-2-ethylhexanoate di-p-methoxycinnamate, trisbiphenyl triazine, p-aminobenzoic acid and esters thereof, 4-tert-butyl-4'-methoxydibenzoylmethane, 4-(2-β-glucopyranosiloxy) propoxy-2-hydroxybenzophenone, octyl salicylate, methyl 2,5-diisopropylcinnamate, 2-[4-(diethylamino)-2-hydroxybenzoyl]benzoic acid hexyl ester cinoxate, dihydroxydimethoxybenzophenone, sodium dihydroxydimethoxybenzophenone disulfonate, dihydroxybenzophenone, dimethicodiethyl benzal malonate, 1-(3,4-dimethoxyphenyl)-4,4-dimethyl-1,3-pentanedione, 2-ethylhexyl dimethoxybenzylidene dioxoimidazolidine propionate, tetrahydroxybenzophenone, terephthalylidene dicamphor sulfonic acid, 2,4,6-tris[4-(2-ethylhexyloxycarbonyl)anilino]-1,3,5-triazine, methylbis(trimethylsiloxy)silyl isopentyl trimethoxycinnamate, drometrizole trisiloxane, amyl p-dimethylaminobenzoate, 2-ethylhexyl p-dimethylaminobenzoate, a mixture of isopropyl p-methoxycinnamate and diisopropyl cinnamic acid ester, 2-ethylhexyl p-methoxycinnamate, 2,4-bis-[{4-(2-ethylhexyloxy)-2-hydroxy}-phenyl]-6-(4-methoxyphenyl)-1,3,5-triazine, 2-hydroxy-4-methoxybenzophenone, hydroxymethoxybenzophenonesulfonic acid and a trihydrate thereof, sodium hydroxymethoxybenzophenone sulfonate, phenylbenzimidazolesulfonic acid, ferulic acid, and 2,2'-methylenebis(6-(2H-benzotriazol-2-yl)-4-(1, 1,3,3-tetramethylbutyl)phenol).

Examples of the antioxidant include: dibutylhydroxytoluene (labeling name: BHT); butylhydroxyanisole (labeling name: BHA), vitamin E, such as δ-tocopherol, and derivatives thereof; thiotaurine; an *Oenothera biennis* extract; β-carotene; a catechin compound; a flavonoid compound; and a polyphenol compound. The catechin compound may be used as a green tea extract or the like.

Examples of the antiseptic/antibacterial agent include parabens, such as isopropylparaben and benzylparaben, benzoic acid, benzoic acid salts, alkyldiaminoethylglycine hydrochloride, a photosensitizer, chlorocresol, chlorobutanol, salicylic acid, salicylic acid salts, sorbic acid and salts thereof, dehydroacetic acid and salts thereof, trichloro hydroxydiphenyl ether (also known as triclosan), p-hydroxybenzoic acid esters and sodium salts thereof, phenoxyethanol, phenol, sodium lauryldiaminoethylglycine, resorcin, zinc-ammonia-silver composite substituted zeolite, panthenyl ethyl ether benzoate, isopropylmethylphenol, cetylpyridinium chloride, benzalkonium chloride, benzethonium chloride, chlorhexidine hydrochloride, orthophenyl phenol, sodium orthophenyl phenol, silver-copper zeolite, chlorhexidine gluconate, cresol, chloramine T, chloroxylenol, chlorphenesin, chlorhexidine, 1,3-dimethylol-5,5-dimethylhydantoin, alkylisoquinolinium bromide, thianthol, and thymol.

Examples of the fragrance include: terpenes and terpenoids, such as citral, menthol, camphor, salvinorin A, cannabinoid, hinokitiol, limonene, farnesol, and vitamin A; aromatic alcohols, such as phenoxyethanol, and phenols, such as eugenol and shogaol; esters, such as butyric acid esters and propionic acid esters; lactones, such as γ-nonalactone and γ-undecalactone; and aldehydes each having 6 to 20 carbon atoms.

The chemical agent may be used as it is, or may be used by being dissolved or dispersed in any of various solvents.

The composition containing an additive for a chemical agent, which contains the additive for a chemical agent of the present invention and the chemical agent, may also be one aspect of the present invention. The composition containing an additive for a chemical agent may contain only one kind, or two or more kinds of the additives for chemical agents of the present invention, and may contain only one kind, or two or more kinds of the chemical agents. In the composition containing an additive for a chemical agent, the use amount of the additive for a chemical agent of the present invention with respect to the chemical agent is not particularly limited, but is, for example, preferably from 0.001 part by weight to 100 parts by weight with respect to 1 part by weight of the chemical agent.

EXAMPLES

The present invention is specifically described below by way of Examples, but the present invention is not limited to these Examples. "Part(s)" means "part(s) by weight" and "%" means "wt %" unless otherwise specified.

<Measurement of Average Particle Diameter in State of Having been Dried Under Reduced Pressure of 0.02 MPa or Less at 100° C. for 1 Hour>

A 50% cumulative value of a volume distribution measured with a dry particle diameter distribution measurement apparatus (manufactured by the Malvern division of Spectris Co., Ltd., model: Mastersizer 3000, dry) was adopted as an average particle diameter in a state of having been dried under a reduced pressure of 0.02 MPa or less at 100° C. for 1 hour. Measurement conditions are shown below.

(Measurement Conditions)

Dry laser diffraction scattering method
Dispersing pressure: 2.0 bar
Venturi: HE Venturi
Particle refractive index: 1.52
Particle absorptivity: 0.01
Particle density: 1.05 g/cm$^3$
Particle shape: non-spherical
Solvent name: air
Measurement range: from 0.1 µm to 3,500 µm <Measurement of Average Particle Diameter of Swelled Body Obtained by Swelling with Deionized Water>

A 50% cumulative value of a volume distribution measured with a wet particle diameter distribution measurement apparatus (manufactured by Horiba, Ltd., model: Partica LA-950V2, wet) was adopted as the average particle diameter of a swelled body. Measurement conditions are shown below.

(Measurement Conditions)

Swelled body refractive index: 1.5
Dispersion medium: deionized water
Measurement range: from 0.01 µm to 3,000 µm <Measurement of Solid Content of Polymer>

About 1 g of a polymer was weighed in a weighing vessel (weight: W1 g) having a bottom surface diameter of about 5 cm (weight: W2 g), and was dried by leaving the whole at rest in a constant-temperature dryer at 150° C. for 1 hour. The total of the weighing vessel and the polymer after the drying (weight: W3 g) was measured, and a solid content was determined from the following equation.

Solid content (wt %)=[(W3−W1)/W2]×100

Example 1

A flask having a volume of 300 ml with a stirring device (paddle blade type), a temperature gauge, a reflux condenser, and a nitrogen inlet tube was initially loaded with 100 g of cyclohexane, and heating was performed under a nitrogen atmosphere in an oil bath at 85° C. After the temperature in the flask had become constant, the feeding of dropping components 1 (N-vinylpyrrolidone: 25 g, acrylic acid: 0.025 g, and pentaerythritol triallyl ether: 0.05 g) and dropping components (oil-soluble azo polymerization initiator V-65 (manufactured by FUJIFILM Wako Pure Chemical Corporation): 0.075 g, and heptane: 40 g) was started. The dropping components 1 and the dropping components 2 were weighed and fed at constant rates over 3 hours and 4.5 hours, respectively. A polymer started to be deposited in about 10 minutes from the start of dropping, and its deposition amount gradually increased. After the completion of the feeding of the dropping components 2, heating was further continued for 0.5 hour, and then the flask was cooled to terminate the reaction. The temperature in the flask was between 79° C. and 81° C., and generally tended to increase with the passage of time (median value: 80° C.)

Subsequently, the precipitate that was the polymer was collected by filtering the reaction liquid, and was dried under reduced pressure at 125° C. for 1 hour to provide a crosslinked body. The crosslinked body was obtained as spherical objects having appropriate sizes. Accordingly, decantation and filtration were finished within short periods of time, and the powder was easy to handle because the influences of a flow of air and static electricity were small during its handling. Observation with a microscope found that most of the spherical objects had a diameter of from about 200 µm to about 600 µm, and the average particle diameter of the spherical objects was 460 µm.

When the whole amount of the resultant spherical objects were pulverized with a laboratory pulverizer OML-1 manufactured by Osaka Chemical Co., Ltd., the spherical objects were easily pulverized in about 20 seconds to provide powder of a crosslinked body (1) as fine and uniform powder. The solid content of the resultant crosslinked body (1) was 99%.

The average particle diameter of the resultant crosslinked body (1) in a state of having been dried under a reduced pressure of 0.01 MPa at 100° C. for 1 hour was 20 µm, and the average particle diameter of a swelled body obtained by swelling the crosslinked body with deionized water was 2 µm. The reason why the average particle diameter of the swelled body is smaller than the average particle diameter of the powder is conceivably because simultaneously with the swelling of the powder through absorption of water, its aggregation was loosened to approach a state of primary particles.

Example 2

A particulate crosslinked body (C1) obtained in Comparative Example 1 to be described later was more finely pulverized with a target-type jet mill to provide powder of a crosslinked body (2) as fine and uniform powder. The solid content of the resultant crosslinked body (2) was 97%.

The average particle diameter of the resultant crosslinked body (2) in a state of having been dried under a reduced pressure of 0.01 MPa at 100° C. for 1 hour was 4 µm, and the average particle diameter of a swelled body obtained by swelling the crosslinked body with deionized water was 6 µm.

Comparative Example 1

130.0 Parts of N-vinylpyrrolidone, 0.52 part of triallyl cyanurate serving as a crosslinking agent, and 304.6 parts of deionized water were loaded into a desktop kneader (manufactured by Chuorika Co., Ltd, model: PNV-1H). Then, nitrogen purging was performed at 100 ml/min for 30 minutes. Then, nitrogen was introduced at 30 ml/min, and the temperature was increased to 56° C. After the liquid temperature had been stabilized at 56° C., 1.96 parts of a 15 wt % aqueous solution of 2,2'-azobis[2-(2-imidazolin-2-yl)propane] dihydrochloride serving as a polymerization initiator was added to initiate polymerization. The polymerization reaction progressed to produce a gel, and then, while the gel was disintegrated by rotating the blade of the kneader, aging was performed at 90° C. for 60 minutes to complete the polymerization. Then, 65.0 parts of a 1 wt % aqueous solution of malonic acid was added over 3 minutes, and the whole was stirred at 90° C. for 60 minutes. Further, 32.5 parts of a 2 wt % aqueous solution of diethanolamine was added over 3 minutes, and the whole was stirred for 30 minutes. Then, the resultant gel was dried at 120° C. for 2 hours to provide a crosslinked body. Then, the resultant crosslinked body was pulverized with a pulverizer until the pulverized product passed through a JIS standard sieve having an aperture of 500 μm. Thus, the particulate crosslinked body (C1) was obtained. The solid content of the resultant crosslinked body (C1) was 97%.

The average particle diameter of the resultant crosslinked body (C1) in a state of having been dried under a reduced pressure of 0.01 MPa at 100° C. for 1 hour was 320 μm, and the average particle diameter of a swelled body obtained by swelling the crosslinked body with deionized water was 195 μm.

[Evaluation of Persistence of Sensation of Coolness and Feeling of Application]

In accordance with blending shown in Table 1, a predetermined amount of l-menthol was added to and dissolved in anhydrous ethanol. To the solution, in accordance with the blending shown in Table 1, any one of the crosslinked body (1), the crosslinked body (2), and the crosslinked body (C1) was added, or none thereof was added, and the solution was stirred to uniformity using a disper. Further, in accordance with the blending shown in Table 1, anhydrous ethanol and purified water were added, and the whole was stirred to uniformity using a disper to prepare evaluation liquids A to D.

TABLE 1

| Raw material | Raw material blending amounts in each evaluation liquid (%) | | | |
|---|---|---|---|---|
| | A | B | C | D |
| l-Menthol | 0.20 | 0.20 | 0.20 | 0.20 |
| Anhydrous ethanol | 20.00 | 20.00 | 20.00 | 20.00 |
| Crosslinked body (1) | — | 2.00 | — | — |
| Crosslinked body (2) | — | — | 2.00 | — |
| Crosslinked body (C1) | — | — | — | 2.00 |
| Anhydrous ethanol | 40.00 | 40.00 | 40.00 | 40.00 |
| Purified water | 39.80 | 37.80 | 37.80 | 37.80 |
| Total | 100.00 | 100.00 | 100.00 | 100.00 |

In accordance with the following procedure, sensory evaluation by humans was performed. The prepared evaluation liquids were each loaded into an eye drop container, and two drops were dropped onto an evaluation site and thinly spread with a hand to check feeling of application, directly followed by the checking of a sensation of coolness. The evaluation site was first set to the back of a hand, and when the sensation of coolness was difficult to feel, was changed to the inside of a forearm. Different samples were applied to a right hand and a left hand, and were compared to each other as to which sample gave a more persistent sensation of coolness. The sample that gave the longer sensation of coolness was compared to still another sample to determine the sample that gave the most persistent sensation of coolness. The number of evaluators was 10. The evaluation results of the persistence of the sensation of coolness are shown in Table 2, and the evaluation results of the feeling of application are shown in Table 3.

It was found from Table 2 that the crosslinked body (1), the crosslinked body (2), and the crosslinked body (C1) each had an effect of exhibiting high persistence of the sensation of coolness, and of those, the crosslinked body (1) had a particularly high effect.

It was found from Table 3 that the crosslinked body (1) received the highest evaluation for the feeling of application, followed by the crosslinked body (2) and the crosslinked body (C1) in order of higher evaluation for the feeling of application.

TABLE 2

| Description | Number of evaluators |
|---|---|
| The evaluation liquid B gave the longest sensation of coolness. | 5 |
| The evaluation liquid B and the evaluation liquid C gave similar degrees of sensation of coolness for long periods of time. | 3 |
| The evaluation liquid B, the evaluation liquid C, and the evaluation liquid D gave similar degrees of sensation of coolness for long periods of time. | 2 |

TABLE 3

| Evaluation liquid | Judgment | Reason | Number of evaluators |
|---|---|---|---|
| A | X | The evaluation liquid flowed on the skin because of a lack of thickening, and hence application was difficult. | 10 |
| B | ◎ | The feeling of application was good, and application was easy. | 10 |
| C | ○ | The viscosity of the evaluation liquid was felt to be nonuniform during application. | 6 |
| | | The evaluation liquid was felt to contain soft particulate matter. | 2 |
| | | The feeling of application was good, and application was easy. | 2 |
| D | Δ | The evaluation liquid was felt to contain particulate matter. | 10 |

[Bactericidal Test]

An in vitro bactericidal test was performed as described below. First, the crosslinked body (1), the crosslinked body (C1), and phenoxyethanol (manufactured by FUJIFILM Wako Pure Chemical Corporation) were used to prepare 10 ml each of such compositions as shown in Table 4. In Table 4, PVP means polyvinylpyrrolidone, and PE means phenoxyethanol. Next, *Escherichia coli* was cultured using Mueller-Hinton agar medium (manufactured by FUJIFILM Wako Pure Chemical Corporation) at 35° C. for 18 hours. Colonies that had appeared were scraped and suspended in Butterfield's buffer (0.0425 g/L potassium dihydrogen phosphate buffer, adjusted to a pH of 7.2), and the suspension was adjusted to about $10 \times 10^8$ CFU/L. 0.5 ml of the bacterial suspension was added to each of the compositions of Table 4, and the whole was subjected to inversion mixing for about 10 seconds and then incubated at 25° C. After 1 hour, after 24 hours, and after 1 week, sampling was performed from each of the compositions, and dilution series were prepared using Butterfield's buffer and applied to Mueller-Hinton agar medium, followed by culture. The number of surviving bacterial cells was counted from the number of colonies that had appeared. The bacterial strain used was *Escherichia coli*, NBRC-3972.

The results of the test revealed that, as shown in Table 4, the crosslinked body (1) alone, the crosslinked body (2)

alone, and phenoxyethanol alone each showed only a low bactericidal property, but the compositions each using the crosslinked body (1) and phenoxyethanol in combination, and the compositions each using the crosslinked body (2) and phenoxyethanol in combination each accelerated the reduction of the number of bacterial cells, thereby showing a synergistic effect.

The judgment in Table 4 was made as follows: a sample that reduced the number of bacterial cells by 4 or more orders of magnitude in 1 week was marked with Symbol "⊚"; a sample that reduced the number of bacterial cells by from 3 orders of magnitude to 2 orders of magnitude was marked with Symbol "0"; a sample that reduced the number of bacterial cells by 1 order of magnitude was marked with Symbol "A"; and a sample that showed no reduction in number of bacterial cells was marked with Symbol

TABLE 4

| | Cross-linked body (1) | Cross-linked body (2) | Phenoxy-ethanol | Pre-mixing | Judgment |
|---|---|---|---|---|---|
| Composition 1 | — | — | — | — | X |
| Composition 2 | — | — | 0.3 wt % | — | X |
| Composition 3 | 1 wt % | — | — | — | Δ |
| Composition 4 | — | 1 wt % | — | — | X |
| Composition 5 | 1 wt % | — | 0.3 wt % | Water + PVP (cross-linked body) | ⊚ |
| Composition 6 | 1 wt % | — | 0.3 wt % | PE + PVP (cross-linked body) | ⊚ |
| Composition 7 | — | 1 wt % | 0.3 wt % | Water + PVP (cross-linked body) | ⊚ |
| Composition 8 | — | 1 wt % | 0.3 wt % | PE + PVP (cross-linked body) | ⊚ |

[Blending of Cosmetic Lotion]

In blending amounts shown in Table 5, (1) to (5) were blended, and uniformly dissolved at 60° C. To the solution, in a blending amount shown in Table 5, (6) that had been heated to 60° C. was gradually added, and the mixture was emulsified using a homogenizer and cooled to 40° C. to give an emulsion. Further, the emulsion was added to a uniformly mixed liquid of (7) to (10) in blending amounts shown in Table 5, and the materials were uniformly mixed. As a result, blendability was satisfactory.

TABLE 5

| | Raw material | Blending amount (wt %) |
|---|---|---|
| (1) | Purified water | 40.90 |
| (2) | 1,3-Butylene glycol | 6.00 |
| (3) | Glycerin | 2.00 |
| (4) | Methylparaben | 0.10 |
| (5) | Polyglyceryl-10 laurate | 1.0 |
| (6) | Cyclopentasiloxane | 10.0 |
| (7) | Purified water | 24.8 |

TABLE 5-continued

| | Raw material | Blending amount (wt %) |
|---|---|---|
| (8) | Crosslinked body (1) (10% solution) | 10.00 |
| (9) | Carbopol Ultrez 10 (Carbomer) (2% aqueous solution) | 5.00 |
| (10) | Sodium hydroxide (10% aqueous solution) | 0.20 |
| | Total | 100.0 |

[Blending of Ionic Compound (Sodium Ascorbyl Phosphate)]

In blending amounts shown in Table 6, (2) was dissolved in (1), then any one of (3) to (5) was gradually added, and the materials were uniformly mixed using a homogenizer. Further, a separately prepared uniform mixture of (6), (7), and (8) in blending amounts shown in Table 6 was added, and the materials were uniformly mixed using a homogenizer to prepare blends (1), (2), and (C1). In addition, in blending amounts shown in Table 6, (2) was dissolved in (1), and then, without the addition of any of (3) to (5), a separately prepared uniform mixture of (6), (7), and (8) in blending amounts shown in Table 6 was added, followed by uniform mixing using a homogenizer to prepare a blend (C2). As shown in Table 6, the blends (1) and (2) using the crosslinked bodies (1) and (2), respectively, each provided a uniform chemical agent having an appropriate viscosity as compared to the blend (C1) using the crosslinked body (C1) and the blend (C2) using none of the crosslinked bodies (1), (2), and (C1). Further, feeling of application was checked, and as a result, it was found that the blends (1) and (2) using the crosslinking bodies (1) and (2), respectively, were smooth, but the blend (C1) using the crosslinking body (C1) was felt to contain grains, and hence was not smooth. The viscosity was measured using a B-type viscometer manufactured by Toki Sangyo Co., Ltd. (model: BM-2, rotor No. 3, number of revolutions: 60 RPM, measurement time: 60 seconds, measurement temperature: 25° C.)

TABLE 6

| | | Blending amounts in each blend (wt %) | | | |
|---|---|---|---|---|---|
| | Raw material | (1) | (2) | (C1) | (C2) |
| (1) | Purified water | 63.25 | 63.25 | 63.25 | 63.25 |
| (2) | Sodium ascorbyl phosphate | 1.0 | 1.0 | 1.0 | 1.0 |
| (3) | Crosslinked body (1) | 0.25 | — | — | — |
| (4) | Crosslinked body (2) | — | 0.25 | — | — |
| (5) | Crosslinked body (C1) | — | — | 0.25 | — |
| (6) | Carbopol Ultrez 10 (Carbomer) (2% aqueous solution) | 25.0 | 25.0 | 25.0 | 25.0 |
| (7) | Sodium hydroxide (1% aqueous solution) | 10.0 | 10.0 | 10.0 | 10.0 |
| (8) | Phenoxyethanol-S | 0.5 | 0.5 | 0.5 | 0.5 |
| | Total | 100.0 | 100 | 100.0 | 100.0 |
| | Viscosity (Pa · s) | 1,300 | 1,340 | 280 | 230 |
| | Feeling | Smooth | Smooth | Grains are felt | — |

INDUSTRIAL APPLICABILITY

The additive for a chemical agent of the present invention is suitably used for, for example, a cosmetic, a fragrance, an aromatic, a deodorant, a pharmaceutical, an insect repellent, an insecticide, and an agricultural chemical.

The invention claimed is:

1. An additive for a chemical agent, comprising a polymer (I) containing 50 mol % to 100 mol % of a structural unit derived from an N-vinyl lactam-based monomer with respect to 100 mol % of structural units derived from all monomers, the additive for a chemical agent having an average particle diameter of 100 μm or less in a state of having been dried under a reduced pressure of 0.02 MPa or less at 100° C. for 1 hour, wherein:

the polymer (I) has a crosslinked structure derived from a crosslinking agent, the crosslinking agent is at least one kind selected from the group consisting of pentaerythritol tetraallyl ether, pentaerythritol triallyl ether, pentaerythritol diallyl ether, and (di, tri, tetra, penta, hexa, hepta, and octa) allyl sucroses, and an average particle diameter of a swelled body obtained by swelling the additive for a chemical agent with deionized water is 2 μm or less.

2. The additive for a chemical agent according to claim 1, wherein the polymer (I) contains 70 mol % to 100 mol % of the structural unit derived from an N-vinyl lactam-based monomer with respect to 100 mol % of the structural units derived from all monomers.

3. The additive for a chemical agent according to claim 1, wherein the polymer (I) has an other structural unit in addition to the structural unit derived from an N-vinyl lactam-based monomer, the other structural unit is a structural unit derived from an other monomer different from the N-vinyl lactam-based monomer, and the content of the structural unit derived from the other monomer in the polymer (I) is from 0 mol % to 50 mol % with respect to 100 mol % of the structural units derived from all monomers.

4. The additive for a chemical agent according to claim 3, wherein the other monomer is at least one kind selected from the group consisting of:

1) (meth)acrylic acid esters comprising methyl (meth)acrylate, ethyl (meth)acrylate, butyl (meth)acrylate, and cyclohexyl (meth)acrylate;

2) hydroxyethyl (meth)acrylate, hydroxypropyl (meth)acrylate, 3-(meth)allyloxy-1,2-dihydroxypropane, (meth)allyl alcohol, isoprenol, and unsaturated alcohols each obtained by adding an alkylene oxide to a hydroxyl group of any such compound;

3) (meth)acrylamide, and derivatives of (meth)acrylamide comprising N-monomethyl (meth)acrylamide, N-monoethyl (meth)acrylamide, and N,N-dimethyl (meth)acrylamide;

4) basic unsaturated monomers comprising dimethylaminoethyl (meth)acrylate, dimethylaminoethyl (meth)acrylamide, vinylpyridine, and vinylimidazole, and salts or quaternized products thereof;

5) vinylamides comprising vinylformamide, vinylacetamide, and vinyloxazolidone; and 6) carboxyl group-containing unsaturated monomers comprising (meth)acrylic acid, itaconic acid, maleic acid, and fumaric acid, and salts thereof.

5. The additive for a chemical agent according to claim 1, wherein a content of a structural unit derived from the crosslinking agent in the polymer (I) is from 0.001 mol % to 10 mol % with respect to 100 mol % of the structural units derived from all monomers.

* * * * *